United States Patent [19]

Patsch et al.

[11] Patent Number: 5,041,631

[45] Date of Patent: Aug. 20, 1991

[54] PROCESS FOR THE PREPARATION OF 2-ALKYLAMINO-4-AMINOBENZENESULFONIC ACIDS

[75] Inventors: Manfred Patsch, Wachenheim; Klaus Pandl, Ludwigshafen, both of Fed. Rep. of Germany

[73] Assignee: BASF Aktiengesellschaft, Ludwigshafen, Fed. Rep. of Germany

[21] Appl. No.: 591,364

[22] Filed: Sep. 20, 1990

[30] Foreign Application Priority Data

Sep. 20, 1989 [DE] Fed. Rep. of Germany ....... 3931326

[51] Int. Cl.$^5$ .......................................... C07C 143/58
[52] U.S. Cl. ................................................... 562/58
[58] Field of Search ........................................ 562/58

[56] References Cited

U.S. PATENT DOCUMENTS

| | | | |
|---|---|---|---|
| 2,575,027 | 10/1949 | Schmidt | 260/510 |
| 2,687,431 | 10/1950 | Marschall | 260/509 |
| 2,727,062 | 12/1955 | Tulagin | 260/509 |
| 3,223,727 | 12/1965 | Stryker | 260/510 |

FOREIGN PATENT DOCUMENTS

| | | | |
|---|---|---|---|
| 0285972 | 10/1988 | European Pat. Off. | 562/58 |
| 0315045 | 5/1989 | European Pat. Off. | |
| 0315046 | 5/1989 | European Pat. Off. | |

OTHER PUBLICATIONS

Organikum 17th Ed., p. 201, 1988.
Methoden der Organischen Chemie, vol. 11/1; pp. 207-212, H. Glaser et al., "Stickstoff-Verbindungen II", 1957.

*Primary Examiner*—Jose G. Dees
*Assistant Examiner*—Porfirio Nazario
*Attorney, Agent, or Firm*—Oblon, Spivak, McClelland, Maier & Neustadt

[57] ABSTRACT

A process for the preparation of 2-alkylamino-4-aminobenzenesulfonic acids by acylation of 2,4-diaminobenzenesulfonic acid followed by alkylation of the resulting 4-acylamino-2-aminobenzenesulfonic acid and, finally, removal of the acyl group by hydrolysis.

3 Claims, No Drawings

PROCESS FOR THE PREPARATION OF 2-ALKYLAMINO-4-AMINOBENZENESULFONIC ACIDS

The present invention relates to a novel process for the preparation of 2-alkylamino-4-aminobenzenesulfonic acids by acylation of 2,4-diaminobenzenesulfonic acid followed by alkylation of the resulting 4-acylamino-2-aminobenzenesulfonic acid and, finally, removal of the acyl group by hydrolysis.

The prior German Patent Applications P 3,914,650.2 and P 3,927,068.8 describe processes for the preparation of N-alkylated phenylenediaminesulfonic acids.

It is an object of the present invention to provide a novel process for the preparation of monoalkylated phenylenediaminesulfonic acids which produces the desired products in a simple manner and in good yield.

We have now found that the preparation of phenylenediaminesulfonic acids of formula I

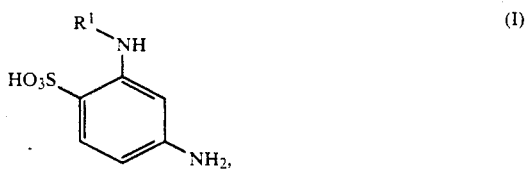

in which $R^1$ denotes $C_1$–$C_4$-alkyl. is advantageously effected by treating 2,4-diaminobenzenesulfonic acid in a first stage with an acylating agent derived from a $C_2$–$C_8$-alkanoic acid and reacting the resulting acyl derivative of formula II

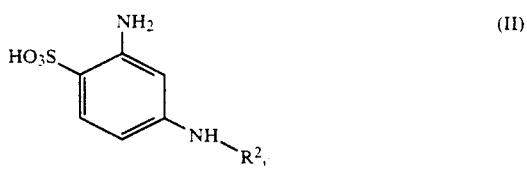

in which $R^2$ denotes $C_2$–$C_3$-alkanoyl, in a second stage, with an alkylating agent of formula III in which $R^1$ has the meaning stated above and X stands for a leaving group, optionally in the presence of an alkali metal halide or alkali metal sulfate, to form a phenylenediamine derivative of formula IV

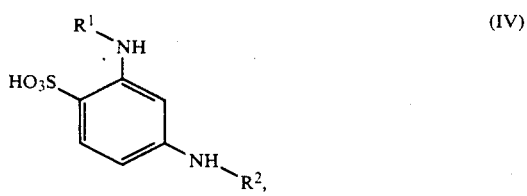

in which $R^1$ and $R^2$ have the meanings stated above, and, in a third stage, hydrolytically removing the $C_2$–$C_8$-alkanoyl radical.

The fact that alkylation reactions on basic nitrogen atoms are highly non-selective is well known (*Organikum*, 17th Edition, page 201). Thus the reaction of a primary amino compound with an alkylating agent such as an alkyl halide or dialkyl sulfate produces not only the secondary amine but also large quantities of tertiary or even quaternary amino compounds before the reaction of the educt has reached completion.

It is therefore frequently necessary, in order to prepare secondary amines in a pure state, to operate with elaborate reaction stages, for example the introduction of a suitable protective group for the nitrogen atom to be alkylated (cf. *Organikum* loc. cit. for example) and hydrolytic removal of the protective group after alkylation has taken place, or the separation of the secondary amine in the form of a sparingly soluble nitrosamine from the reaction solution followed by hydrolytic purification of the isolated nitrosamine (cf. Houben-Weyl, *Methoden der Organischen Chemie*, Vol. 11/1, pp. 207-212).

It was thus surprising to find that straightforward monoalkylation of the $NH_2$-group takes place in the process proposed in the present invention.

The process of the invention is generally carried out by first reacting 2,4-diaminobenzenesulfonic acid with the acylating agent in aqueous reaction medium.

The said acylating agents derived from a $C_2$–$C_8$-alkanoic acid, are usually the corresponding carboxylic anhydrides or mixtures of such carboxylic anhydrides or the corresponding carboxylic halides. Examples of such agents are acetic anhydride, propionic anhydride, acetyl chloride or propionyl chloride. We prefer to use propionic anhydride or acetic anhydride, particularly the latter.

For each mole of 2,4-diaminobenzenesulfonic acid there will normally be used from 1.0 to 1.5, preferably from 1.05 to 1.15, moles of acylating agent. Acylation generally takes place at a temperature of from 10° to 45° C., preferably from 20° to 40° C., and at pH of from 3 to 7.5.

On completion of conversion, which generally takes from 1 to 6 hours, the acylating agent of formula II can be precipitated using, say, common salt, at a pH of from 0.5 to 7.5. Alternatively the reaction solution can be further processed as it is.

The phenylenediamine derivative of formula IV is obtained by reacting the acylation product II with an alkylating agent of formula III

$$R^1-X \qquad (III),$$

in which $R^1$ is $C_1$–$C_4$-alkyl and X is a leaving group, optionally in the presence of an alkali metal halide or alkali metal sulfate, in which case the use of an alkali metal chloride or alkali metal sulfate is to be preferred.

Suitable leaving groups X are, for example, halogen such as chlorine, bromine or iodine, or a radical of the formula $O-SO_2-C_6H_5$, $O-SO_2-C_6H_4-CH_3$ or $O-SO_2-OR^3$, where $R^3$ stands for $C_1$–$C_4$-alkyl. The use of $C_1$–$C_4$-dialkyl sulfates, particularly dimethyl sulfate, is preferred.

The alkylation is carried out in known manner in aqueous reaction medium. For each mole of acylation product II there will generally be used from 1.0 to 3.0, preferably from 1.1 to 2.1, moles of alkylating agent III. The pH of the reaction solution is usually from 2.0 to 10.0 and preferably from 3.5 to 7.0 and can be adjusted to the desired range, if necessary, by the addition of a base such as sodium or potassium hydroxide, sodium or potassium carbonate or bicarbonate or sodium acetate.

The reaction temperature is usually from 10° to 50° C. If dimethyl sulfate is used, the preferred temperature is 10°–30° C.

In a preferred embodiment, alkylation of the acyl derivative of formula II in the second stage is effected at an initial concentration of acyl derivative II of from 0.5 to 1.7 moles per liter of reaction mixture.

In a particularly preferred embodiment of the process, from 50 to 250 g of an alkali metal chloride or alkali metal sulfate are added to the reaction mixture before commencement of alkylation, for each mole of acyl derivative II. Examples of suitable salts are lithium chloride, sodium chloride, potassium chloride, sodium sulfate, potassium sulfate, sodium hydrogensulfate and potassium hydrogensulfate, the use of sodium or potassium chloride or sodium sulfate being particularly significant.

The reaction is advantageously carried out by adding the alkylating agent to the reaction solution over a period of from 30 minutes to 5 hours.

The reaction product IV can be isolated by simple filtration at a pH of from 0 to 7, optionally preceded by the addition of a salt. Alternatively, the $C_2$-$C_8$-alkanoyl group be hydrolytically removed in situ. This may be effected in an acidic or alkaline aqueous medium, acid hydrolysis being preferred. Examples of suitable media are hydrochloric acid, an aqueous sulfuric acid solution, caustic soda solution and caustic potash solution.

Under either acid or alkaline conditions, the hydrolytic cleavage is effected with heating under reflux. Cleavage is complete after from 2 to 3 hours, after which the target product can be isolated by known methods.

The novel process, which can be operated continuously or batchwise, produces phenylenediaminesulfonic acids of formula I in a simple manner. These are valuable intermediates in the synthesis of dyes such as reactive dyes as described in EP-A 315,045 or EP-A 315,046.

The invention is illustrated below by the following Examples.

EXAMPLE 1

235 g of 2,4-diaminobenzesulfonic acid were dissolved in 1000 ml of water adjusted to pH 7 by the addition of caustic soda solution. To this solution there were added 84 g of sodium bicarbonate and 53 g of sodium carbonate and, over a period of 5 hours at 25° C., 162 g of acetic anhydride. Stirring was continued for 1 hour, after which 162 g of sodium chloride were added, 332 g of dimethyl sulfate were then metered to the solution at from 30° to 35° C. Stirring was continued for 30 minutes and the pH was adjusted to from 0 to 0.5 with hydrochloric acid. The mixture was heated under reflux for 3 hours and then cooled with stirring, adjusted to pH 1.0 with caustic soda solution and filtered.

Yield: 202 g of 2-methylamino-4-aminobenzenesulfonic acid.

EXAMPLE 2

1.88 kg of 2,4-diaminobenzenesulfonic acid were dissolved in 2.5 l of water adjusted to pH 7 by the addition of caustic soda solution. 1.08 kg of acetic anhydride were added dropwise over 3 hours at 20° C. The pH was adjusted to 7 with caustic soda solution, after which 0.17 kg of sodium bicarbonate and 0.9 kg of sodium sulfate were added. 1.6 kg of dimethyl sulfate were then metered to the solution at 25° C. Stirring was continued for 30 minutes and the pH was adjusted to 0 with hydrochloric acid. The mixture was then diluted with 3.5 l of water, heated under reflux for 3 hours and cooled with stirring. The pH was adjusted to 0.5 with caustic soda solution and the reaction mixture was filtered.

Yield: 1.55 kg of 2-methylamino-4-aminobenzenesulfonic acid.

We claim:

1. A process for the preparation of a phenylenediaminesulfonic acid of formula I

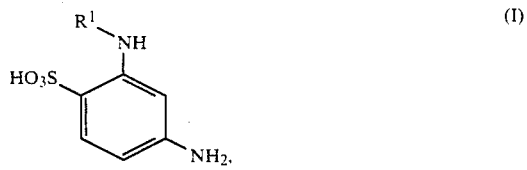

in which $R^1$ denotes $C_1$-$C_4$-alkyl,
wherein 2,4-diaminobenzenesulfonic acid is treated in a first stage with an acrylating agent derived from a $C_2$-$C_8$-alkanoic acid, and the resulting acyl derivative of formula II

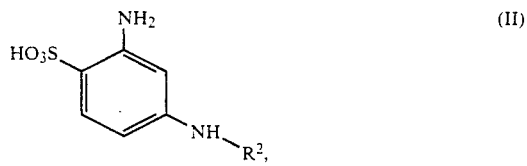

in which $R^2$ denotes $C_2$-$C_8$-alkanoyl,
is reacted, in a second stage, with an alkylating agent of formula III

in which $R^1$ has the meaning stated above and X stands for a leaving group,
optionally in the presence of an alkali metal halide or alkali metal sulfate, to form a phenylenediamine derivative of formula IV

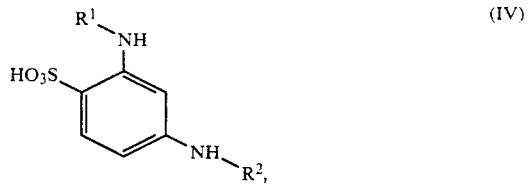

in which $R^1$ and $R^2$ have the meanings stated above,
and, in a third stage, the $C_2$-$C_8$-alkanoyl radical is removed by hydrolysis.

2. A process as claimed in claim 1, wherein alkylation of the acyl derivative of formula II in the second stage is effected at an initial concentration of acyl derivative II of from 0.5 to 1.7 moles per liter of reaction mixture.

3. A process as claimed in claim 1, wherein from 50 to 250 g of an alkali metal chloride or alkali metal sulfate are added to the reaction mixture before commencement of alkylation, for each mole of acyl derivative II.

* * * * *